United States Patent
Kupper

(10) Patent No.: US 7,939,543 B2
(45) Date of Patent: May 10, 2011

(54) METHOD OF REDUCING α, β UNSATURATED KETONES IN OPIOID COMPOSITIONS

(75) Inventor: Robert J. Kupper, East Greenwich, RI (US)

(73) Assignee: Purdue Pharma L.P., Stamford, CT (US)

( * ) Notice: Subject to any disclaimer, the term of this patent is extended or adjusted under 35 U.S.C. 154(b) by 840 days.

(21) Appl. No.: 11/885,402

(22) PCT Filed: Feb. 27, 2006

(86) PCT No.: PCT/EP2006/001798
§ 371 (c)(1),
(2), (4) Date: Sep. 28, 2007

(87) PCT Pub. No.: WO2006/094672
PCT Pub. Date: Sep. 14, 2006

(65) Prior Publication Data
US 2008/0132702 A1    Jun. 5, 2008

Related U.S. Application Data

(60) Provisional application No. 60/658,791, filed on Mar. 4, 2005.

(51) Int. Cl.
*A61K 31/485*    (2006.01)
*C07D 489/04*    (2006.01)

(52) U.S. Cl. ............................. 514/282; 546/45; 546/44

(58) Field of Classification Search .................. 514/282; 546/45, 44
See application file for complete search history.

(56) References Cited

U.S. PATENT DOCUMENTS

| 3,812,312 | A | 5/1974 | Andersen et al. | 200/61.53 |
| 6,008,355 | A | 12/1999 | Huang et al. | 546/45 |
| 6,177,567 | B1 | 1/2001 | Chiu et al. | 546/47 |
| 7,129,248 | B2 * | 10/2006 | Chapman et al. | 514/282 |

FOREIGN PATENT DOCUMENTS

| EP | 0889045 | 7/1999 |
| WO | 2005097801 | 10/2005 |

OTHER PUBLICATIONS

Pasto, et al. "Organic Reactions," vol. 40, p. 91-155, (1991).
Proksa, et al. "10-Hydroxythebaine," Arch. Pharm. Pharm. Med. Chem., 332, 369-370 (1999).
KraBnig, R. et al., "Optimization of the Synthesis of Oxycodone and 5-Methyloxycodone," *Arch. Pharm. Med. Chem.* vol. 329, pp. 325-326, 1996.
Weiss, U., "Derivatives of Morphine II[1]. Demethylation of 14-hydroxycodeinone, 14-Hydroxymorphinone and 8, 14-Dihydroxydihydromorphinone," *Deritatives of Morphine II*, vol. 22, pp. 1505-1508, 1957.
Coop, A., et al. "A Novel Synthesis of Thebaine from Codeine," *Heterocycles*, vol. 49, 1998.
Coop, A. et al. "Studies into the Direct Oxidation of Codeine to 14-Hydroxycodeinone," *Tetrahedron*, vol. 55, pp. 11429-11436, 1999.
Bari, S. et al., "Impurity profile: Significance in Active Pharmaceutical Ingredient," *Eurasian Journal of Analytical Chemistry*, vol. 2, pp. 31-53, 2007.
Statutory Declaration of Paul William Jones in connection of Australian Patent Application No. 2005230826 dated Dec. 8, 2010.
Statutory Declaration of Philip Marshall filed on Jul. 27, 2010, in connection with the opposition in corresponding Australian Application No. 2005230826.

* cited by examiner

*Primary Examiner* — Charanjit S Aulakh
(74) *Attorney, Agent, or Firm* — Davidson, Davidson & Kappel LLC

(57) ABSTRACT

The present invention is directed to a process for reducing the level of α, β-unsaturated ketone in an opioid analgesic composition by hydrogenation the opioid analgesic composition with diimide or a diimide progenitor.

22 Claims, No Drawings

US 7,939,543 B2

METHOD OF REDUCING α, β UNSATURATED KETONES IN OPIOID COMPOSITIONS

FIELD OF THE INVENTION

The present invention relates to a process for reducing the amount of α, β-unsaturated ketones in opioid preparations.

BACKGROUND OF THE INVENTION

Opioid agonists exert an agonist effect at specific, saturable opioid receptors in the CNS and other tissues. In man, opioid agonists may produce any of a variety of effects including analgesia.

Thebaine, a compound derived from opium, although having no medicinal use in itself, is useful as a starting material in synthetic schemes for the production of many opioid agonists, e.g., oxycodone. In other schemes, codeine can be utilized as the starting material for the production of many opioids, α, β-unsaturated ketones are a precursor to the opioid analgesic in many synthetic pathways. For example, 14-hydroxycodeinone is a precursor to oxycodone. Accordingly, an amount of α, β-unsaturated ketone is present as an impurity in opioid analgesic compositions.

Methods of producing thebaine or 14-hydroxy substituted opium derivatives have been reported, e.g. in U.S. Pat. No. 3,894,026 and U.S. Pat. No. 4,045,440.

The oxidation of codeine to codeinone, an initial step in the synthesis of opium derivatives has been reported in EP 0889045, U.S. Pat. No. 6,008,355, and in the J. Am. Chem. Soc, 1051, 73, 4001 (Findlay).

The reaction of codeinone to unsaturated ketone has been reported in U.S. Pat. No. 6,008,355, and in Tetrahedron 55, 1999 (Coop and Rice).

The methylation of codeinone to thebaine has been reported in Heterocycles, 1988, 49, 43-7 (Rice), and EP0889045.

U.S. Pat. No. 6,177,567 describes the hydrogenation of unsaturated ketone to oxycodone by reduction with diphenylsilane and Pd(Ph3P)/ZnC12 or with sodium hypophosphite in conjunction with a Pd/C catalyst in aqueous acetic acid.

Krabnig et al. in "Optimization of the Synthesis of Oxycodone and 5-Methyloxycodone" Arch. Pharm. (1996), 329 (6), (325-326) describes hydrogenating a solution of unsaturated ketone in glacial acetic acid with a Pd—C-catalyst at 30 psi at the described conditions.

There is a continuing need in the art to provide improved methods for hydrogenating α, β-unsaturated ketones to produce the corresponding saturated ketone.

All references cited herein are incorporated by reference in their entireties for all purposes.

OBJECTS AND SUMMARY OF THE INVENTION

It is an object of certain embodiments of the present invention to provide a process for reducing the impurity level of α, β-unsaturated ketone in an opioid analgesic composition (e.g., oxycodone hydrochloride API).

It is an object of certain embodiments of the present invention to provide a process for converting an α, β-unsaturated ketone composition (e.g., a 14-hydroxy-codeinone composition) to a corresponding saturated ketone composition (e.g., an oxycodone composition).

It is an object of certain embodiments of the present invention to provide a process for reducing the level of α, β-unsaturated ketone as an impurity in an opioid analgesic composition (e.g., oxycodone hydrochloride API) by hydrogenating the composition with diimide (H—N=N—H) or a diimide progenitor (e.g., dipotassium azodicarboxylate).

It is an object of certain embodiments of the present invention to provide a process for converting an α, β-unsaturated ketone composition to a corresponding saturated ketone composition (e.g., converting a unsaturated ketone composition to an oxycodone composition) by hydrogenation with diimide or a diimide progenitor.

In preferred embodiments, the process of the present invention provides an opioid analgesic composition having an α, β-unsaturated ketone level of less than 25 ppm, less than about 15 ppm, less than about 10 ppm, or less than about 5 ppm.

In certain embodiments, the invention is directed to a process for preparing an opioid analgesic composition having an α, β-unsaturated ketone level of less than 25 ppm comprising hydrogenating an opioid composition having an α, β-unsaturated ketone level of more than 100 ppm with diimide or a diimide progenitor to reduce the amount of α, β-unsaturated ketone to a level of less than 25 ppm, less than about 15 ppm, less than about 10 ppm, or less than about 5 ppm.

In certain embodiments, the invention is directed to a process for preparing an opioid analgesic composition comprising hydrogenating an α, β-unsaturated ketone composition with diimide or a diimide progenitor to produce an opioid analgesic composition having a level of α, β-unsaturated ketone of less than 25 ppm, less than about 15 ppm, less than about 10 ppm, or less than about 5 ppm.

In all of the embodiments disclosed herein, the resultant opioid analgesic composition can be further hydrogenated with diimide or a diimide progenitor to further decrease the amount of α, β-unsaturated ketone.

In one embodiment, the starting material is an opioid analgesic composition comprising α, β-unsaturated ketone in an amount of 100 ppm or higher, and the final opioid analgesic composition has an α, β-unsaturated ketone level of less than 25 ppm, less than about 15 ppm, less than about 10 ppm, or less than about 5 ppm (e.g., about 2 ppm). In another embodiment, the starting material is an opioid analgesic composition comprising α, β-unsaturated ketone in an amount of between 15 ppm and 25 ppm, and the final opioid analgesic composition has an α, β-unsaturated ketone level of less than about 10 ppm, or less than about 5 ppm (e.g., about 2 ppm). In another embodiment, the starting material is an opioid analgesic composition comprising α, β-unsaturated ketone in an amount of between 10 ppm and 25 ppm, and the final opioid analgesic composition has an α, β-unsaturated ketone level of less than about 5 ppm.

In certain embodiments, the process further comprises recovering the resultant opioid analgesic composition.

In certain embodiments, the invention is directed to a process for preparing an opioid analgesic composition comprising hydrogenating a starting opioid analgesic composition having an α, β-unsaturated ketone impurity with diimide or a diimide progenitor under reflux, wherein the resultant opioid analgesic composition has a level of α, β-unsaturated ketone less than the level in the starting composition.

In certain embodiments, the opioid analgesic composition produced by the process of the present invention has a lower limit of 0.25 ppm, 0.5 ppm, 1 ppm, 2 ppm or 5 ppm of α, β-unsaturated ketone.

The term "ppm" as used herein means "parts per million". As used to refer to α, β-unsaturated ketone, "ppm" means parts per million of α, β-unsaturated ketone in a particular sample.

A method of determining the level of α, β-unsaturated ketone in an oxycodone preparation can be performed in accordance with commonly assigned U.S. Provisional Application Ser. No. 60/557,502 filed Mar. 30, 2004, commonly assigned U.S. Provisional Application Ser. No. 60/648,629 filed Jan. 31, 2005, entitled "Methods For Detecting 14-Hydroxycodeinone and Codeinone."

DETAILED DESCRIPTION

The diimide required to carry out the hydrogenation step of the process of the present invention can be added directly to the reaction medium or can result from the inclusion of a diimide progenitor such as dipotassium azodicarboxylic acid. In certain embodiments, decomposition of the dipotassium salt of azodicarboxylic acid with a weak acid (such as formic acid, acetic acid or oxalic acid) produces the diimide in situ. The dipotassium salt can be obtained by hydrolysis of azodicarboxylic acid diamide, azodicarboxylic acid dimethyl ester or azodicarboxylic acid diethyl ester with aqueous potassium hydroxide solution.

In certain embodiments, the dipotassium salt can be suspended in an alcohol (preferably methanol, ethanol or isopropanol) or in a polar ether (such as tetrahydrofuran, dioxane, glycol monomethyl ether or glycol dimethyl ether). The opioid analgesic or α, β-unsaturated ketone can be added to the suspension, and the reaction mixture can be acidified at a reaction temperature ranging from about 0 degrees C. to about 80 degrees C. Reaction times can be, e.g., from about 5 to about 120 minutes. In certain embodiments, the diimide is used in excess, e.g., from about 3 to about 20 moles per mole of opioid analgesic or α, β-unsaturated ketone.

One benefit of the process of the present invention is that by-products of the reaction (e.g., potassium chloride, carbon dioxide and nitrogen) are non-toxic.

In certain embodiments, the present invention is directed to a process for reducing the amount of α, β-unsaturated ketone in an opioid analgesic composition (e.g., oxycodone hydrochloride API) by hydrogenating the opioid analgesic composition with diimide or a diimide progenitor. In certain embodiments, the opioid analgesic is a compound of formula (I):

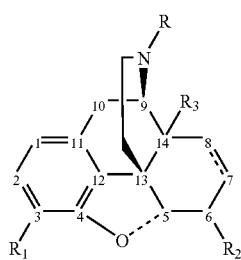

(I)

wherein
R is selected from the group consisting of hydrogen; $C_{1-8}$ alkyl; $C_{3-6}$cycloalkyl; $(C_{3-6})$cycloalkyl$(C_{1-3})$alkyl; phenyl $(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_1$ is selected from the group consisting of hydrogen; $C_{1-8}$ alkyl; $C_{3-6}$cycloalkyl; $C_{1-8}$alkoxy; $C_{3-6}$cycloalkoxy; 2-(4-morpholinyl)ethyl; benzyloxycarbonyl; $(Rs)_3C(O)$—; phenyl$(C_{1-3})$alkyl; and phenyl$(C_{1-3})$alkyl substituted with 1-3 members of the group consisting Of $C_{1-8}$ alkyl, trifluoromethyl, nitro, dialkylamino and cyano;

$R_2$ is selected from the group consisting of hydrogen; oxo; hydroxyl; $C_{1-8}$ alkyl; d-salkoxy; $C_{3-6}$cycloalkyl; and $C_{3-6}$ cycloalkoxy; and $R_3$ is hydrogen; hydroxyl; or alkoxy;

$R_8$ is independently hydrogen, a $C_{1-4}$ alkyl, a $C_{3-6}$ cycloalkyl, phenyl or benzyl wherein $R_2$ is oxo when the bond at position 7-8 is saturated;

or a pharmaceutically acceptable salt thereof.

In certain embodiments, the present invention is directed to a process for converting an α, β-unsaturated ketone composition to an opioid analgesic composition by hydrogenation with diimide or a diimide progenitor. In certain embodiments, the α, β-unsaturated ketone is a compound of formula (II):

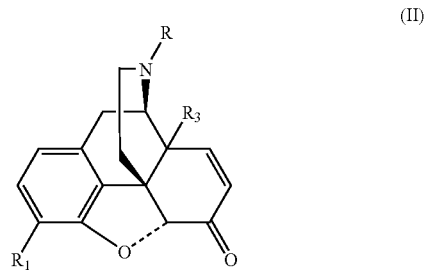

(II)

wherein:
R is selected from the group consisting of hydrogen; $C_{1-8}$ alkyl; $C_{3-6}$cycloalkyl; $(C_{3-6})$cycloalkyl$(C_{1-3})$alkyl; phenyl $(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_1$ is selected from the group consisting of hydrogen; $C_{1-8}$alkyl; $C_{3-6}$cycloalkyl; $C_1$-salkoxy; $C_{3-6}$cycloalkoxy; 2-(4-morpholinyl)ethyl; benzyloxycarbonyl; $(R_8)_3C(O)$—; phenyl$(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_3$ is hydrogen, hydroxyl or alkoxy;

$R_8$ is independently hydrogen, a $C_{1-4}$ alkyl, a $C_{3-6}$ cycloalkyl, phenyl or benzyl or a pharmaceutically acceptable salt thereof.

In certain embodiments, the present invention is directed to a process for reducing the amount of α, β-unsaturated ketone in an opioid analgesic composition by hydrogenating the opioid analgesic composition with diimide or a diimide progenitor wherein the opioid analgesic is a compound of formula (III):

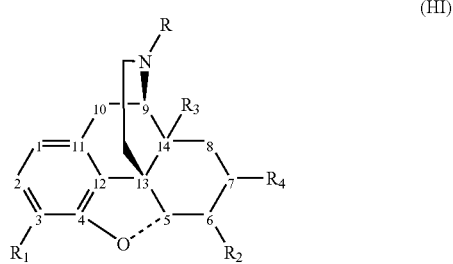

(III)

wherein
R is selected from the group consisting of hydrogen; $C_{1-8}$ alkyl; $C_{3-6}$cycloalkyl; $(C_{3-6})$cycloalkyl$(C_{1-3})$alkyl; phenyl ($C_{1-3}$)alkyl; and phenyl($C_{1-3}$)alkyl substituted with 1-3 members of the group consisting of $C_{1-8}$ alkyl, trifluoromethyl, nitro, dialkylamino and cyano;

$R_1$ is selected from the group consisting of hydrogen; $C_{1-8}$alkyl; $C_{3-6}$cycloalkyl; Q-salkoxy; $C_{3-6}$cycloalkoxy; 2-(4-morpholinyl)ethyl; benzyloxycarbonyl; $(Rs)_3C(O)$—; phenyl($C_{1-3}$)alkyl; and phenyl($C_{1-3}$)alkyl substituted with 1-3 members of the group consisting of $C_{1-8}$ alkyl, trifluoromethyl, nitro, dialkylamino and cyano;

$R_2$ is selected from the group consisting of hydrogen; oxo; hydroxyl; $C_{1-8}$ alkyl; Q^alkoxy; $C_{3-6}$cycloalkyl; $C_{3-6}$cycloalkoxy; and $R_4$ is hydrogen; hydroxyl; alkoxy; $C_{1-8}$alkyl substituted with 1-3 members of the group consisting of $C_{1-8}$ alkyl, hydroxyl, cyano, nitro and dialkylamino;

$R_8$ is independently hydrogen, a $C_{1-4}$ alkyl, a $C_{3-6}$ cycloalkyl, phenyl or benzyl or a pharmaceutically acceptable salt thereof.

In certain embodiments, the opioid analgesic of the present invention is selected from the group consisting of oxycodone, hydromorphone, hydrocodone, codeine, morphine, buprenorphine, pharmaceutically acceptable salts thereof, and mixtures thereof.

In certain embodiments, the α, β-unsaturated ketone is selected from the group consisting of 14-hydroxycodeinone; morphinone; codeinone; 7-acetyl-7,8-didehydro-6,14-endo-ethanoltetrahydrothebaine; 7,8-didehyronaloxone; 7,8-didehydronatrexone; 7,8-didehyroxymorphone; salts thereof; and mixtures thereof.

In certain embodiments, the hydrogenation is carried out at a pressure from about 5 PSIG to about 200 PSIG, or from about 40 PSIG to about 60 PSIG.

In certain embodiments, the hydrogenation is carried out at a temperature from about 20° C. to about 100° C., or from about 40° C. to about 85° C.

In certain embodiments, the hydrogenation is carried out at a pH of less than 5, less than 3, or less than 1, e.g., about 0.5.

In certain embodiments, the total reaction time of the hydrogenation reaction is for a duration sufficient to reduce the content of the α, β-unsaturated ketone to a level of less than 25 ppm, less than about 15 ppm, less than about 10 ppm, or less than about 5 ppm. The actual reaction time can vary depending upon the temperature and efficiency of the hydrogenation system. Depending on the hydrogenation conditions (e.g., temperature and pressure), the total reaction time to achieve the desired reduction in α, β-unsaturated ketone can be, e.g., from about 10 minutes to about 36 hours.

The reaction may be carried out in a solvent such as water; an alcohol (such as, e.g., isopropanol, methanol or ethanol); tetrahydrofuran; an aromatic hydrocarbon (such as benzene); an ether (such as dioxane); an ester of an alkanoic acid (such as methyl acetate or ethyl acetate); an amide (such as, e.g., dimethylformamide, diethylformamide, dimethylacetomide, or other N-alkyl substituted lower fatty acid amides); furfural; N-methylpyrrolidone; formylmorpholine; β-methoxypropionitrile; or an appropriate mixture of any two or more of the aforementioned solvents.

The following examples illustrate various aspects of the present invention. They are not to be construed to limit the claims in any manner whatsoever.

Prophetic Examples of Diimide Reductions

Into a jacketed 250 mL flask fitted with magnetic stirrer, addition funnel, jacket chiller and $N_2$ sweep is placed 3.13 g (10.0 mmoles) of 14-hydroxy-codeinone 20 mL of water and 13.8 g (300 mmoles) of formic acid. The resulting clear stirred solution is then chilled to 5-10° C. and a solution of 19.4 g (100 mmoles) of dipotassium azodicarboxylate in 25 mL of water is carefully added over a 2 hr period. This solution is stirred until gas evolution ceases. The solution is then adjusted to pH~10 by the addition of 25% aqueous ammonia. After stirring for 1 hr at 5-10° C. the white solid is collected and washed with several portions of water. The white solid is then suspended in 15 mL of 2-propanol at 80° C. and made distinctly acidic by the addition of 37% aqueous hydrochloric acid. The clear solution is then allowed to cool to room temperature followed by chilling to 0-5° C. The resulting white crystals are collected on a filter and washed with 2-propanol 10 mL. The moist solid is then dried in vacuo at 50° C. in a moist $N_2$ stream to give oxycodone hydrochloride mono hydrate free of olefinic impurity.

The diimide reducing agent may also be generated from hydrazine or hydrazine hydrate in the presents of $O_2$, $H_2O_2$ or air in the presences a copper catalyst such as copper(II)acetate or sulfate or iron complexes such as potassium ferrocyanide. Other transition metals could also be used.

The α-βunsaturated ketones are not good substrates for diimide reductions and thus very large excesses are required, however, ketones are generally not reduced and the reagents are inexpensive making this a viable procedure. The procedure with out limitation may be applied to all members of this class of compounds.

What is claimed is:

1. A process for reducing a level of α, β-unsaturated ketone in an opioid analgesic composition comprising hydrogenating a starting opioid analgesic composition having an α, β-unsaturated ketone impurity with diimide, a diimide progenitor, or a combination thereof in a suitable solvent, to produce a resultant opioid analgesic composition having a level of α, β-unsaturated ketone less than the starting composition, wherein the opioid analgesic is selected from the group consisting of oxycodone, hydrocodone, hydromorphone, pharmaceutically acceptable salts thereof and mixtures thereof.

2. The process of claim 1, wherein the diimide progenitor is dipotassium azodicarboxylate.

3. The process of claim 1, wherein said hydrogenation is performed under reflux.

4. The process of claim 1, wherein the solvent is an alcohol, selected from the group consisting of methanol, ethanol and isopropanol.

5. The process of claim 1, further comprising recovering the hydrogenated opioid analgesic composition.

6. The process of claim 1, wherein the opioid analgesic is oxycodone or a pharmaceutically acceptable salt thereof.

7. The process of claim 1, wherein the opioid analgesic is hydrocodone or a pharmaceutically acceptable salt thereof.

8. The process of claim 1, wherein the opioid analgesic is hydromorphone or a pharmaceutically acceptable salt thereof.

9. The process of claim 1, wherein the hydrogenation produces an opioid analgesic composition having an α, β-unsaturated ketone level of less than 25 ppm, less than about 15 ppm, less than about 10 ppm, or less than about 5 ppm.

10. The process of claim 1, wherein the α, β-unsaturated ketone is a compound of formula (II):

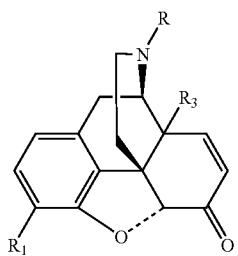 (II)

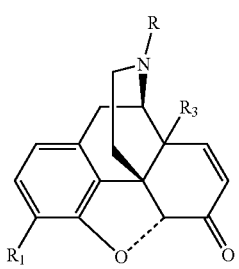 (II)

wherein:
R is selected from the group consisting of hydrogen; $C_{1-8}$ alkyl; $C_{3-6}$cycloalkyl; $(C_{3-6})$cycloalkyl$(C_{1-3})$alkyl; phenyl$(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_1$ is selected from the group consisting of hydrogen; $C_{1-8}$alkyl; $C_{3-6}$cycloalkyl; $C_{1-8}$alkoxy; $C_{3-6}$cycloalkoxy; 2-(4-morpholinyl)ethyl; benzyloxycarbonyl; $(R_8)_3C(O)$—; phenyl$(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_3$ is hydrogen, hydroxyl or alkoxy;
each $R_8$ is independently hydrogen, a $C_{1-4}$ alkyl, a $C_{3-6}$ cycloalkyl, phenyl or benzyl or a pharmaceutically acceptable salt thereof.

11. A process for producing an opioid analgesic composition comprising
hydrogenating an α, β-unsaturated ketone composition, with diimide, a diimide progenitor or a combination thereof in a suitable solvent, to form the opioid analgesic composition,
wherein the opioid analgesic is selected from the group consisting of oxycodone, hydrocodone, hydromorphone, pharmaceutically acceptable salts thereof and mixtures thereof.

12. The process of claim 11, wherein the diimide progenitor is dipotassium azodicarboxylate.

13. The process of claim 11, wherein said hydrogenation is performed under reflux.

14. The process of claim 11, wherein the solvent is an alcohol selected from the group consisting of methanol, ethanol and isopropanol.

15. The process of claim 11, further comprising recovering the hydrogenated opioid analgesic composition.

16. The process of claim 11, wherein the α, β-unsaturated ketone is a compound of formula (II):

wherein:
R is selected from the group consisting of hydrogen; $C_{1-8}$ alkyl; $C_{3-6}$cycloalkyl; $(C_{3-6})$cycloalkyl$(C_{1-3})$alkyl; phenyl$(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_1$ is selected from the group consisting of hydrogen; $C_{1-8}$alkyl; $C_{3-6}$cycloalkyl; $C_{1-8}$alkoxy; $C_{3-6}$cycloalkoxy; 2-(4-morpholinyl)ethyl; benzyloxycarbonyl; $(R_8)_3C(O)$—; phenyl$(C_{1-3})$alkyl; and phenyl$(C_{1-3})$alkyl substituted with 1-3 members of the group consisting of $C_{1-8}$ alkyl, trifluoromethyl, nitro, dialkylamino and cyano;

$R_3$ is hydrogen, hydroxyl or alkoxy;
each $R_8$ is independently hydrogen, a $C_{1-4}$ alkyl, a $C_{3-6}$ cycloalkyl, phenyl or benzyl or a pharmaceutically acceptable salt thereof.

17. The process of claim 16, wherein the opioid analgesic is hydromorphone or a pharmaceutically acceptable salt thereof.

18. The process of claim 16, wherein the opioid analgesic is hydrocodone or a pharmaceutically acceptable salt thereof.

19. The process of claim 11, wherein the opioid analgesic is oxycodone or a pharmaceutically acceptable salt thereof.

20. The process of claim 11, wherein the hydrogenation produces an opioid analgesic composition having an α, β-unsaturated ketone level of less than 25 ppm, less than about 15 ppm, less than about 10 ppm, or less than about 5 ppm.

21. The process of claim 5, wherein the recovery step comprises crystallizing the hydrogenated opioid analgesic composition.

22. The process of claim 15, wherein the recovery step comprises crystallizing the hydrogenated opioid analgesic composition.

\* \* \* \* \*